United States Patent [19]

Lavielle et al.

[11] Patent Number: 4,605,647
[45] Date of Patent: Aug. 12, 1986

[54] OXAAZAPHOSPHORINE COMPOUNDS AND PHARMACEUTICAL COMPOSITIONS

[75] Inventors: Gilbert Lavielle; Claude Cudennec, both of La Celle St Cloud, France

[73] Assignee: ADIR, S.A.R.L., Neuilly-sur-Seine, France

[21] Appl. No.: 752,365

[22] Filed: Jul. 5, 1985

[30] Foreign Application Priority Data

Jul. 6, 1984 [FR] France ................... 84 10731

[51] Int. Cl.⁴ .................. A61K 31/66; A61K 31/675; C07F 9/24; C07F 9/65
[52] U.S. Cl. ................................. 514/85; 514/89; 514/90; 514/91; 514/110; 544/157; 544/337; 546/21; 548/412; 558/81
[58] Field of Search ............... 544/157, 337; 546/21; 548/412; 260/923, 936; 514/85, 89, 90, 91, 110

[56] References Cited

U.S. PATENT DOCUMENTS 4,239,709 12/1980 Sato ................... 260/936

FOREIGN PATENT DOCUMENTS 59-29696 2/1984 Japan .
59-31787 2/1984 Japan .

Primary Examiner—Robert W. Ramsuer
Attorney, Agent, or Firm—Gordon W. Hueschen

[57] ABSTRACT

New oxaazaphosphorine compounds corresponding to the formula:

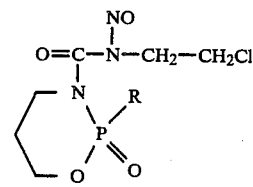

in which R is
  alkyl, cycloalkyl or alkoxy,
  phenyl, phenylalkyl, phenoxy or thiophenoxy in which the phenyl ring may be substituted by alkyl or alkoxy or by halogen.
  mono- or di-alkylamino optionally mono- or di-substituted by halogen, or
  pyrrolidinyl, piperidyl or morpholinyl or optionally substituted piperazinyl.

These compounds may be used for antineoplastic therapy especially in the treatment of tumors.

8 Claims, No Drawings

OXAAZAPHOSPHORINE COMPOUNDS AND PHARMACEUTICAL COMPOSITIONS

The present invention relates to new oxaazaphosphorine compounds a process for the preparation thereof and pharmaceutical compositions containing them.

Oxaazaphosphorines are known from the literature and are used therapeutically, especially in anti-cancer chemotherapy, and one of the most widely used antitumor drugs, cyclophosphamide (Angew. Chem. 70, 539, 1958) is a nitrogen mustard ($N-(CH_2-CH_2-Cl)_2$) grafted directly onto the phosphorus atom of an oxaazaphosphorine heterocycle. This heterocycle not only acts as the vector of the alkylating agent but also plays an important and complex biological role in the activation of the molecule.

Japanese Patent Application Nos. 141 308 (13.08.1982) and 141 309 (13.08.1982) describe 2-oxo-2-(N-nitroso-2-haloethylamino)-oxaazaphosphorines in which the properties of the heterocycle are used as the vector of another alkylating radical which is also attached to the phosphorus atom.

Other alkylating agents, the nitrosoureas, are also used in anti-cancer therapeutics but it is known that nitrosoureas that are mono-substituted at the nitrogen atom decompose spontaneously in solution after activation by removal of the proton on the nitrogen atom. On the other hand, nitrosoureas that are di-substituted at the nitrogen atom are stable in solution but are generally inactive (J. Med. Chem. 27, 97, 1984.).

The aim of the present invention is to provide nitrosoureas that are stable in solution but also active in vivo and in vitro.

The aim is achieved by preparing 2-oxo-2H-tetrahydro-1,3,2-oxaazaphosphorine compounds corresponding to the general formula I:

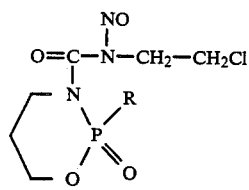

in which R is selected from the group consisting of:
straight-chain and branched-chain alkyl groups containing from 1 to 6 carbon atoms inclusive,
cycloalkyl groups containing from 3 to 7 carbon atoms inclusive,
an unsubstituted phenyl group and phenyl groups substituted by, a radical selected from the group consisting of alkyl and alkoxy radicals each containing from 1 to 4 carbon atoms inclusive and halogen atoms.
phenylalkyl groups containing from 7 to 10 carbon atoms inclusive, and these radicals substituted on the phenyl ring by a substituent selected from the group consisting of halogen atoms and alkyl and alkoxy radicals each containing from 1 to 4 carbon atoms inclusive,
straight-chain and branched-chain alkoxy groups containing from 1 to 4 carbon atoms inclusive,
phenoxy and thiophenoxy groups,
mono- and di-alkylamino groups containing from 1 to 8 carbon atoms inclusive and these groups mono- and di-substituted by halogen atoms, and
pyrrolidin-1-yl, morpholin-4-yl and piperid-1-yl groups, an unsubstituted piperazin-1-yl group and piperazin-1-yl groups substituted in the 4-position, by a substituent selected from the group consisting of straight-chain and branched-chain alkyl radicals containing from 1 to 4 carbon atoms inclusive, cycloalkyl groups containing from 5 to 7 carbon atoms inclusive, an unsubstituted phenyl group and unsubstituted phenylalkyl groups containing from 7 to 10 carbon atoms inclusive, and these phenyl and phenylalkyl groups substituted on the aromatic ring, by a substituent selected from the group consisting of halogen atoms and straight-chain and branched-chain alkyl and alkoxy radicals each containing from 1 to 4 carbon atoms inclusive, and also, when R represents a piperzinyl group, their pharmaceutically acceptable acid addition salts (hydrochlorides, sulfates, methanesulfonates, oxalates, fumarates, maleates . . . ).

The currently preferred compounds are compounds of the general formula I in which R represents an amino group or, especially, a pyrrolidinyl, piperidyl or morpholinyl radical or an optionally substituted piperazinyl radical.

The present invention also relates to the preparation of the compounds of the formula I, characterised in that a phosphonic or phosphoric acid dichloride of the formula II

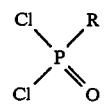

in which R has the same meaning as in formula I, is condensed with 3-aminopropan-1-ol in an inert solvent and in the presence of an acid acceptor at a temperature of from $-30°$ to $0°$ C. to form a compound of the formula III

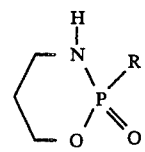

in which R has the same meaning as in formula I, and which is condensed with an excess of $\beta$-chloroethyl isocyanate of the formula IV

either directly, when R represents an amino group, or, when R is not an amino group, after previously activating the nitrogen atom of the 1,3,2-oxaazaphosphorine ring by means of butyllithium in a basic solvent, such as tetrahydrofuran, the reaction with butyllithium being carried out at a temperature of from $-70°$ to $-40°$ C., to form a compound of the formula V

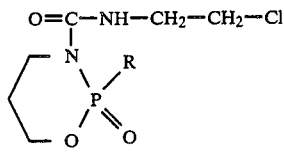

in which R has the same meaning as in formula I, and which is then nitrosated in an acidic or basic medium by the action of nitrosating agents, such as nitrosyl chloride, sodium nitrite, nitrogen tetroxide, etc. . . . to form a compound of the formula I, which, when R is a piperazinyl group, can then be converted into its pharmaceutically acceptable acid addition salt.

In order to carry out the nitrosation, it is advantageous previously to activate the compounds of the formula V by treating them, for example, with one equivalent of butyllithium in tetrahydrofuran at a temperature of −80° C.

The starting materials of the formula II are prepared in accordance with the methods described in the literature, and especially in Methoden der organischen Chemie, Houben Weyl—fourth edition, Phosphorverbindungen I & II, Georg Thieme Verlag 1963.

The following Examples illustrate the invention and do not limit it in any way. The melting points were determined on a Kofler hot block. The NMR spectra were obtained using tetramethylsilane as the internal reference and deuterated chloroform as the solvent. The physico-chemical and spectral characteristics of the compounds mentioned as examples are listed in Table I.

EXAMPLE 1

3-[N-(2-chloroethyl)-N-nitrosoamido]-2-isopropyl-2-oxo-2H-tetrahydro-1,3,2-oxaazaphosphorine

STAGE A 2-isopropyl-2-oxo-2H-tetrahydro-1,3,2-oxaazaphosphorine 0.1 mole of isopropylphosphonic acid dichloride is added, while stirring, to a solution of 0.1 mole of 3-aminopropan-1-ol and 0.2 mole of triethylamine in 200 cm$^3$ of dichloromethane cooled to −20° C. The reaction mixture is stirred for 1 hour at ambient temperature, the precipitate is filtered off and the mother liquors are washed twice, each time with 50 cm$^3$ of water saturated with sodium chloride.

The organic phase is removed, dried and evaporated, and there are obtained 14.5 g of 2-isopropyl-2-oxo-2H-tetrahydro-1,3,2-oxaazaphosphorine which are used without further purification in the following stage.

STAGE B

3-[N-(2-chloroethyl)-amido]-2-isopropyl-2-oxo-2H-tetrahydro-1,3,2-oxaazaphosphorine The 14.5 g of 2-isopropyl-2-oxo-2H-tetrahydro-1,3,2-oxaazaphosphorine obtained in the previous stage are introduced into a vessel containing 150 cm$^3$ of tetrahydrofuran; the mixture is cooled to −80° C., one equivalent of a solution of butyllithium in hexane is added and the solution is maintained at the above temperature for two hours. Two equivalents of β-chloroethyl isocyanate dissolved in 20 cm$^3$ of tetrahydrofuran are introduced in a single addition. The solution is maintained at a temperature of −50° C. for 15 minutes and is then hydrolysed and extracted 3 times with 100 cm$^3$ of diethyl ether each time. The ethereal solutions are combined, dried and evaporated. The oily residue obtained is taken up in a small amount of isopropanol and the precipitate formed is separated by filtration. The mother liquors are evaporated under reduced pressure and the 14.5 grams of oil obtained are chromatographed on a column of 300 g of silica (solvent=dichloromethane-methanol 98:2).

10 g of 3-[N-(2-chloroethyl)-amido]-2-isopropyl-2-oxo-2H-tetrahydro-1,3,2-oxaazaphosphorine are obtained (yield 42%).

Percentage analysis:

|  | C | H | N | Cl |
|---|---|---|---|---|
| Calculated | 40.23 | 6.75 | 10.43 | 13.20 |
| Found | 39.77 | 6.76 | 10.04 | 13.26 | for $C_9H_{18}ClN_2O_3P = 268.5$

Principal spectral characteristics infra-red: $\nu$NH: 3500 and 3300 cm$^{-1}$;

infra-red: $\nu$C=O: 1680 and 1540 cm$^{-1}$.

nuclear magnetic resonance:

1.1 ppm; 3H; d of d; JPH=2 Hz; JHH=6.3 Hz. 1.4 ppm; 3H; d; JHH=6.3 Hz. 1.7 to 2.7 ppm; 3H, m. 2.8 to 3.5 ppm; 1H, m. 3.6 ppm; 4H; A$_2$B$_2$. 4 to 4.8 ppm; 3H; m. 8.1 ppm; 1H exchangeable; m.

STAGE C

3-[N-(2-chloroethyl)-N-nitrosoamido]-2-isopropyl-2-oxo-2H-tetrahydro-1,3,2-oxaazaphosphorine 5.2 g of the 3-[N-(2-chloroethyl)-amido]-2-isopropyl-2-oxo-2H-tetrahydro-1,3,2-oxaazaphosphorine obtained in the previous stage are introduced into a vessel containing 50 cm$^3$ of tetrahydrofuran. The mixture is cooled to −80° C. and then one equivalent of a solution of butyllithium in hexane is added dropwise and the solution is maintained at −80° C. while stirring. One equivalent of nitrosyl chloride is then introduced rapidly. The green solution obtained rapidly decolorises. When it has decolorised completely, it is hydrolysed at reduced temperature and extracted three times with 50 cm$^3$ of diethyl ether each time. The ethereal fractions are combined, dried and then evaporated. The oil obtained (5.4 g) is rapidly chromatographed on a column of silica (solvent=dichloromethane-acetone 90:10) and the product obtained is crystallised from a small amount of petroleum ether. 4.7 g of 3-[N-(2-chloroethyl)-N-nitrosoamido]-2-isopropyl-2-oxo-2H-tetrahydro-1,3,2-oxaazaphosphorine are obtained (yield 81%).

EXAMPLE 2

3-[N-(2-chloroethyl)-N-nitrosoamido]-2-phenyl-2-oxo-2H-tetrahydro-1,3,2-oxaazaphosphorine

STAGE A 2-phenyl-2-oxo-2H-tetrahydro-1,3,2-oxaazaphosporine

Following the procedure described in Example 1, stage A, starting from 0.41 mole of phenylphosphonic acid dichloride and a mixture of 0.41 mole of 3-aminopropan-1-ol and 0.82 mole of triethylamine in 800 cm$^3$ of dichloromethane, there are obtained 38 g of product which are purified by chromatography on a column of silica (solvent=dichloromethane-methanol 98:2).

30 g of 2-phenyl-2-oxo-2H-tetrahydro-1,3,2-oxaazaphosphorine are obtained.

STAGE B

3-[N-(2-chloroethyl)-amido]-2-phenyl-2-oxo-2H-tetrahydro-1,3,2-oxaazaphosphorine A solution of 25.6 g (0.13 mole) of 2-phenyl-2-oxo-2H-tetrahydro-1,3,2-oxaazaphosphorine in 300 cm³ of tetrahydrofuran is cooled to −80° C., one equivalent of a solution of butyllithium in hexane is added dropwise thereto and the whole is stirred for 30 minutes at −65° C., cooled to −80° C. again and then two equivalents of β-chloroethyl isocyanate dissolved in 25 cm³ of tetrahydrofuran are introduced in a single addition. The reaction mixture is maintained at −80° C. for half an hour, hydrolysed and then extracted three times with 150 cm³ of diethyl ether each time. The ethereal extracts are combined, dried and evaporated and the oily residue obtained is taken up in a small amount of isopropanol. The precipitate is suction-filtered and the mother liquors are evaporated. 32 g of product are collected, of which 12 g are purified by chromatography on a column of silica (solvent=cyclohexane-acetone 70:30) to obtain 6.6 g of pure 3-[N-(2-chloroethyl)-amido]-2-phenyl-2-oxo-2H-tetrahydro-1,3,2-oxaazaphosphorine.

STAGE C

3-[N-(2-chloroethyl)-N-nitrosoamido]-2-phenyl-2-oxo-2H-tetrahydro-1,3,2-oxaazaphosphorine The 6.6 g of 3-[N-(2-chloroethyl)-amido]-2-phenyl-2-oxo-2H-tetrahydro-1,3,2-oxaazaphosphorine obtained in the previous stage are introduced into 75 cm³ of tetrahydrofuran, the whole is cooled to −80° C. and one equivalent of a solution of butyllithium in hexane is added dropwise thereto. The mixture is maintained at −80° C. for one hour while stirring and then one equivalent of nitrosyl chloride is rapidly introduced and the temperature is brought up to −65° C. while continuing to stir. The reaction mixture is hydrolysed and extracted 3 times with 100 cm³ of diethyl ether each time. The combined, dried and concentrated ethereal extracts yield 7.9 g of a yellow oil which is rapidly chromatographed in accordance with the technique described by W. C. STILL (J. Org. Chem. 1978, 43, 2923) (solvent=ether-hexane-methanol 70:25:5). 4.5 g of 3-[N-(2-chloroethyl)-N-nitrosoamido]-2-phenyl-2-oxo-2H-tetrahydro-1,3,2-oxaazaphosphorine are collected and then crystallised from a small amount of diisopropyl ether (yield: 62%).

EXAMPLE 3

3-[N-(2-chloroethyl)-N-nitrosoamido]-2-methoxy-2-oxo-2H-tetrahydro-1,3,2-oxaazaphosphorine

STAGE A

2-methoxy-2-oxo-2H-tetrahydro-1,3,2-oxaazaphosphorine

By replacing the isopropylphosphonic acid dichloride in Example 1, Stage A, by methyl dichlorophosphate, 2-methoxy-2-oxo-2H-tetrahydro-1,3,2-oxaazaphosphorine is obtained (yield 50%). b.p. (0.4 mm/Hg)=140° C.

STAGE B

3-[N-(2-chloroethyl)-amido]-2-methoxy-2-oxo-2H-tetrahydro-1,3,2-oxaazaphosphorine By replacing the 2-phenyl-2-oxo-2H-tetrahydro-1,3,2-oxaazaphosphorine in Example 2, stage B, by 2-methoxy-2-oxo-2H-tetrahydro-1,3,2-oxaazaphosphorine, 3-[N-(2-chloroethyl)-amido]-2-methoxy-2-oxo-2H-tetrahydro-1,3,2-oxaazaphosphorine is obtained in the same manner (yield 58% m.p.=50° C.

Percentage analysis:

|  | C | H | N | Cl |
|---|---|---|---|---|
| Calculated | 32.75 | 5.50 | 10.91 | 13.81 |
| Found | 32.88 | 5.41 | 10.96 | 13.65 | for $C_7H_{14}ClN_2O_4P = 256.632$

Spectral characteristics in:
infra-red: $\nu$NH: 3340 cm$^{-1}$;
infra-red: $\nu$C=O: 1680 and 1535 cm$^{-1}$.

NMR: 1.5 to 2.5 ppm; 2H; m. 2.5 to 3.5 ppm; 1H; m. 3.6 ppm; 4H; $A_2B_2$. 3.8 ppm; 3H, d; JPH=12 Hz. 4.5 ppm; 3H; m. 8 ppm; 1H; m; exchangeable.

STAGE C

3-[N-(2-chloroethyl)-N-nitrosoamido]-2-methoxy-2-oxo-2H-tetrahydro-1,3,2-oxaazaphosphorine By replacing the 3-[N-(2-chloroethyl)-amido]-2-isopropyl-2-oxo-2H-tetrahydro-1,3,2-oxaazaphosphorine in Example 1, stage C, by 3-[N-(2-chloroethyl)-amido]-2-methoxy-2-oxo-2H-tetrahydro-1,3,2-oxaazaphosphorine, there is obtained, after rapid chromatography on silica (cyclohexane-acetone 70:30), 3-[N-(2-chloroethyl)-N-nitrosoamido]-2-methoxy-2-oxo-2H-tetrahydro-1,3,2-oxaazaphosphorine which is crystallised from diisopropyl ether (yield 48%).

EXAMPLE 4

3-[N-(2-chloroethyl)-N-nitrosoamido]-2-[1-(4-methylpiperazinyl)]-2-oxo-2H-tetrahydro-1,3,2-oxaazaphosphorine

STAGE A

2-[1-(4-methylpiperazinyl)]-2-oxo-2H-tetrahydro-1,3,2-oxaazaphosphorine

By replacing the isopropylphosphonic acid dichloride in Example 1, stage A, by N-methylpiperazin-1-yl-phosphoric acid dichloride, 2-[1-(4-methylpiperazinyl)]-2-oxo-2H-tetrahydro-1,3,2-oxaazaphosphorine is obtained which is washed with alkalised water and then with distilled water and is used as it is in the following stage (yield: 79%).

STAGE B

3-[N-(2-chloroethyl)-amido]-2-[1-(4-methylpiperazinyl)]-2-oxo-2H-tetrahydro-1,3,2-oxaazaphosphorine 15 g of the 2-[1-(4-methylpiperazinyl)]-2-oxo-2H-tetrahydro-1,3,2-oxaazaphosphorine obtained in the previous stage are heated at 35° C. for 24 hours in 30 cm³ of β-chloroethyl isocyanate and then evaporated to the greatest extent possible. 28 g of product are obtained which are chromatographed on a column of silica ($CH_2Cl_2$-methanol).

10.7 g of 3-[N-(2-chloroethyl)-amido]-2-[1-(4-methylpiperazinyl)]-2-oxo-2H-tetrahydro-1,3,2-oxaazaphosphorine are isolated (yield 48%).

STAGE C

3-[N-(2-chloroethyl)-N-nitrosoamido]-2-[1-(4-methyl-piperazinyl)]-2-oxo-2H-tetrahydro-1,3,2-oxaazaphosphorine By replacing the 3-[N-(2-chloroethyl)-amido]-2-isopropyl-2-oxo-2H-tetrahydro-1,3,2-oxaazaphosphorine in Example 1, stage C, by 3-[N-(2-chloroethyl)-amido]-2-[1-(4-methylpiperazinyl)]-2-oxo-2H-tetrahydro-1,3,2-oxaazaphosphorine, and adding nitrosyl chloride at a temperature of $-100°$ C. and stirring for 30 minutes at $-90°$ C., an oily residue is obtained which is rapidly chromatographed on silica (acetone-tetrahydrofuran 50:50) to yield pure 3-[N-(2-chloroethyl)-N-nitrosoamido]-2-[1-(4-methylpiperazinyl)]-2-oxo-2H-tetrahydro-1,3,2-oxaazaphosphorine which is then dissolved in a mixture of ethyl acetate and acetone (1:1) and converted into its oxalate by adding the corresponding amount of oxalic acid.

EXAMPLES 5 to 13

By following the procedure described in Example 1 and using the corresponding phosphoric or phosphonic acid dichloride, the following compounds are prepared in the same manner:

(5): 3-[N-(2-chloroethyl)-N-nitrosoamido]-2-methyl-2-oxo-2H-tetrahydro-1,3,2-oxaazaphosphorine (6): 3-[N-(2-chloroethyl)-N-nitrosoamido]-2-(1-methylpropyl)-2-oxo-2H-tetrahydro-1,3,2-oxaazaphosphorine (7): 3-[N-(2-chloroethyl)-N-nitrosoamido]-2-cyclohexyl-2-oxo-2H-tetrahydro-1,3,2-oxaazaphosphorine (8): 3-[N-(2-chloroethyl)-N-nitrosoamido]-2-benzyl-2-oxo-2H-tetrahydro-1,3,2-oxaazaphosphorine (9): 3-[N-(2-chloroethyl)-N-nitrosoamido]-2-phenoxy-2-oxo-2H-tetrahydro-1,3,2-oxaazaphosphorine (10): 3-[N-(2-chloroethyl)-N-nitrosoamido]-2-[(4-chlorophenyl)-methyl]-2-oxo-2H-tetrahydro-1,3,2-oxaazaphosphorine (11): 3-[N-(2-chloroethyl)-N-nitrosoamido]-2-(4-chlorophenyl)-2-oxo-2H-tetrahydro-1,3,2-oxaazaphosphorine (12): 3-[N-(2-chloroethyl)-N-nitrosoamido]-2-(4-methylphenyl)-2-oxo-2H-tetrahydro-1,3,2-oxaazaphosphorine (13): 3-[N-(2-chloroethyl)-N-nitrosoamido]-2-(4-fluorophenyl)-2-oxo-2H-tetrahydro-1,3,2-oxaazaphosphorine

EXAMPLES 14 to 19

By following the procedure described in Example 4 and starting from the corresponding phosphoric acid dichlorides, there are obtained in the same manner the following compounds:

(14): 3-[N-(2-chloroethyl)-N-nitrosoamido]-2-(piperid-1-yl)-2-oxo-2H-tetrahydro-1,3,2-oxaazaphosphorine (15): 3-[N-(2-chloroethyl)-N-nitrosoamido]-2-(morpholin-4-yl)-2-oxo-2H-tetrahydro-1,3,2-oxaazaphosphorine (16): 3-[N-(2-chloroethyl)-N-nitrosoamido]-2-[4-(2-methoxyphenyl)-piperazin-1-yl]-2-oxo-2H-tetrahydro-1,3,2-oxaazaphosphorine hydrochloride (17): 3-[N-(2-chloroethyl)-N-nitrosoamido]-2-[(N,N-bis-2-chloroethyl)-amino]-2-oxo-2H-tetrahydro-1,3,2-oxaazaphosphorine (18): 3-[N-(2-chloroethyl)-N-nitrosoamido]-2-[1-(4-cyclohexylpiperazinyl)]-2-oxo-2H-tetrahydro-1,3,2-oxaazaphosphorine oxalate (19): 3-[N-(2-chloroethyl)-N-nitrosoamido]-2-[1-(4-butylpiperazinyl)]-2-oxo-2H-tetrahydro-1,3,2-oxaazaphosphorine oxalate

Pharmacological study of the compounds of the invention

The compounds of the invention of the general formula I possess valuable pharmacological and therapeutic properties. These derivatives have a high anti-tumor activity. They can therefore be used in the treatment of cancer.

The compounds are tested for their capacity to prolong the survival of mice inoculated intraperitoneally, intramuscularly or intracerebrally with tumour cells in accordance with the guidelines recommended by the National Cancer Institute (USA) (GERAN, R. I. et al. Cancer Chemotherapy Reports, 1972, III, Vol. 3, No. 2, pp. 1 to 87); these tests are recognised as being representative of the anti-tumor effect in humans (DRISCOLL, J. S. Cancer Treatment Reports, 1984, Vol. 68, No. 1, pp. 63 to 85). The cytotoxic strength of the compounds with respect to cancerous cells was also measured by applying the clonogenicity test as codified by SALMON, S. E. and Von HOFF, D. D. (Semin. Oncol., 1981, Vol. 8, p. 3787).

The compounds were found to be capable not only of retarding the growth of tumors transplanted into mice but also of curing animals in which leukaemia had been induced. By way of example, the compound of Example 4 according to the invention, at a dose of 67 micromoles per kg upwards in a single dose or 22 micromoles in multiple doses, causes remissions in mice for more than 60 days after inoculation of the cancerous cells. At the same dose, it prevents the formation of pulmonary metastases resulting from the injection of a carcinoma into the paws.

The compounds according to the invention also have a considerable advantage: the absence of resistance encountered with the nitrosoureas. The failure of anticancer chemotherapies in fact results from the cancerous cell's developing defences which protect it against the destructive action of the anti-cancer agents (CURT, G. A. et al., 1984, Cancer Treat. Rep. 68, p. 87).

The activity of the compounds according to the invention was tested on cell lines selected for their resistance to nitrosoureas (DCT Tumor Bank, Inventory of Transplantable Animal and Human tumors, NCI (USA), June 30, 1981).

As an example, the compound of Example 4 according to the invention prolongs by more than 50% the survival of mice in which leukaemia has been induced by the intraperitoneal inoculation of 100,000 cells of the line L1210/BCNU, while BCNU is not able to prolong their survival to any significant extent (see following Table).

| COMPOUND | ACTIVITY AGAINST THE DEVELOPMENT OF MURINE LEUKAEMIA L1210 RESISTANT TO BCNU | | | | | |
|---|---|---|---|---|---|---|
| | NUMBER OF ANIMALS PER BATCH | UNIT DOSE PER TREATMENT ($\mu$ mole/kg) | NUMBER OF TREAT-MENTS | DAYS OF TREATMENT(S) (DAY) (*) | AVERAGE TIME OF SURVIVAL (DAY) | % INCREASE SURVIVAL TIME/ CONTROL ANIMALS (**) |
| CONTROL(***) | 30 | — | — | — | 9.3 | 0 |
| BCNU | 6 | 138 | 1 | 1 | 11.2 | 20 |
| COMPOUND N°4 | 6 | 84 | 1 | 1 | 14 | 51 |
| — | 6 | 42 | 3 | 1,5,9 | 14.3 | 54 |
| — | 6 | 21 | 9 | 1 to 9 | 14.8 | 59 |

(*)Day 0 of the experiment is the day on which 100,000 L1210/BCNU cells are inoculated intraperitoneally.
(**)The value of 25% is required to prove significant anti-tumour activity on this model.
(***)Control batch = animals inoculated with the tumour and treated only with the administration vehicle (HPC 0.2%, NaCl 0.15M).

In vitro, cancerous cells treated with concentrations as low as 0.5 nanomole per milliliter of the compound of Example 4 according to the invention are incapable of forming colonies of malignant cells, while more than 14 nanomoles per milliliter of N,N'-bis(2-chloroethyl)-N-nitrosourea ("BCNU") (which is the compound in the same therapeutic class that is used the most widely clinically) are required to prevent the formation of colonies of malignant cells. In addition, when the compound according to the invention is maintained in solution in a complete culture medium for more than 3 hours at 37° C., it does not lose any of its cytotoxic properties while, during the same period, the strength of BCNU decreases considerably.

The compounds according to the invention appear to have a low toxicity. By way of example, three intraperitoneal injections of the compound of Example 4 according to the invention, each at an interval of 4 days, into B6D2F1 mice at a dose of 67 micromoles per kg never reduce the number of the leucocytes in the peripheral blood to below 70% of the initial value; at an equipotent dose, BCNU causes the leucocyte level to fall to less than half the normal value. The erythrocyte and thrombopoietic levels are not affected to any significant extent by treatment with the products according to the invention. This excellent property can be correlated with the fact that the compound according to the invention is not able to carbamoylate lysine molecules with which it has been mixed for 6 hours at 37° C.

Indeed it has been maintained (KANN, H. E. 1981, in: NITROSOUREAS: Current Status and New Developments, Prestayko, A. W. et al, editors, Acad. Press. p. 96) that the carbamoylating power of certain nitrosoureas exposes normal tissues to undesirable toxic effects. The compounds according to the invention therefore have the surprising quality of being very active against cancerous cells and, in addition, of being incapable of having an adverse effect on components essential to the survival of normal cells.

The compounds according to the invention can be used in animals in cases of leukaemias, myelomas, carcinomas, sarcomas, melanomas, epitheliomas, gliomas, teratomas and, more generally, of cancers of all locations.

The invention also extends to pharmaceutical compositions containing as active ingredient at least one compound of the general formula I or, optionally, one of its pharmaceutically acceptable acid addition salts, alone or in combination with one or more inert non-toxic excipients suitable for pharmaceutical use. The pharmaceutical compositions obtained in this manner are advantageously in various galenical forms, such as, for example, tablets, dragées, soft gelatin capsules, hard gelatin capsules, cachets, suppositories, injectable or drinkable solutions, or preparations suitable for sublingual administration.

The posology used may vary widely, depending on the age and the weight of the patient, the nature of the location and the severity of the cancerous disease. The preferred administrative route is the oral route, but the rectal and parenteral routes are also suitable. As a rule, the unit dose will preferably be from 5 to 100 mg.

| FORMULATION EXAMPLE | |
|---|---|
| 3-[N—(2-chloroethyl)-N—nitrosoamido]-2-[1-(4-methyl-piperazinyl)]-2-oxo-2H-tetrahydro-1,3,2-oxaazaphosphorine oxalate | 20 mg |
| talc | 5 mg |
| lactose | 25 mg | for one soft gelatin capsule.

TABLE 1

| Compounds No. | R | Yield % | m.p. °C. | IR (cm$^{-1}$) | NMR |
|---|---|---|---|---|---|
| 1 | —CH(CH$_3$)$_2$ | 81 | 84 | $\nu$C=O: 1690 | 1.05 ppm, 3H, d of d ($J_{PH}$ = 2Hz; $J_{HH}$ = 6.3Hz 1.4 ppm, 3H, d, $J_{HH}$ = 6.3Hz 1.9 to 2.8 ppm, 3H, m; 3.2 to 3.8, 3H, m; 4 to 4.7, 5H, m |
| 2 | —C$_6$H$_5$ | 62 | 74 | $\nu$C=O: 1700 | 1.8 to 3 ppm, 2H, m; 3.3 to 3.9 ppm, 3H, m; 3.9 to 4.9 ppm, 5H, m; 7.3 to 8.1 ppm, 5H, m |
| 3 | —OCH$_3$ | 48 | 65 | $\nu$C=O: 1710 | 1.7 to 2.8 ppm, 2H, m; 3.2 to 4.7 ppm, 11H, m; 3.8 ppm, 3H, d, $J_{PH}$ = 11.6 H$_3$ |

TABLE 1-continued

| Compounds No. | R | Yield % | m.p. °C. | IR (cm$^{-1}$) | NMR |
|---|---|---|---|---|---|
| 4 | —N(CH$_2$CH$_2$)$_2$NCH$_3$ (N-methylpiperazinyl), oxalate | 45 | 110 | $\nu$NH+ and OH: 2000 to 3700; $\nu$C=O 1700 | 1.8 to 2.3 ppm, 2H, m; 2.7 ppm, 3H, s; 2.8 to 4.6 ppm, 16H, m; 10.6 ppm, 2H exchangeable |
| 5 | —CH$_3$ | 51 | 105 | $\nu$C=O: 1690 | 1.6 to 1.9 ppm, 3H, d, (J$_{PH}$ = 18Hz); 2 to 2.5 ppm, 2H, m; 3.2 to 3.8 ppm, 3H, m; 4 to 4.8 ppm, 5H, m |
| 6 | —CH(CH$_3$)C$_2$H$_5$ | 43 | oil | $\nu$C=O: 1705 | 0.9 to 1.1 ppm, 3H, m; 1.4 ppm. 3H, d; 1.5 to 2.8 ppm, 5H, m; 3.2 to 4 ppm, 3H, m; 4 to 4.8 ppm, 5H, m |
| 7 | cyclohexyl | 47 | oil | $\nu$C=O: 1705 | 1 to 2.7 ppm, 13H, m; 3.2 to 3.8 ppm, 3H, m; 4 to 4.7 ppm, 5H, m |
| 8 | —CH$_2$—C$_6$H$_5$ | 71 | 99 | $\nu$C=O: 1705 | 1.7 to 3.1 ppm, 3H, m; 3.35 ppm, 2H, d; 3.5 to 4.7 ppm, 7H, m; 7.25 ppm, 5H, s |
| 9 | —O—C$_6$H$_5$ | 60 | oil | $\nu$C=O: 1715; $\nu$C=O: 1590 | 2.1 ppm, 2H, m; 3.2 to 4 ppm, 3H, m; 4 to 5 ppm, 5H, m; 7 to 7.25 ppm, 5H, m |
| 10 | —CH$_2$—C$_6$H$_4$—Cl | 73 | 90 | $\nu$C=O: 1690 | 1.8 to 3.1 ppm, 3H, m; 3.4 ppm, 2H, d; 3.6 ppm, 2H, m; 3.8 to 4.8 ppm, 5H, m; 7.4 ppm, 4H, s |
| 11 | —C$_6$H$_4$—Cl | 33 | 90 | $\nu$C=O: 1710 | 2 to 3 ppm, 2H, m; 3.3 to 4.8 ppm, 8H, m; 7.3 to 8 ppm, 4H, m |
| 12 | —C$_6$H$_4$—CH$_3$ | 30 | 80 | $\nu$C=O: 1700 | 2 to 2.7 ppm, 2H, m; 2.4 ppm, 3H, s; 3.3 to 5 ppm, 8H, m; 7.2 to 8 ppm, 4H, m |
| 13 | —C$_6$H$_4$—F | 80 | 103 | $\nu$C=O: 1700 | 1.8 to 2.6 ppm, 2H, m; 3.3 to 4.8 ppm, 8H, m; 7 to 8.2 ppm, 4H, m |
| 14 | —N(CH$_2$)$_5$ (piperidinyl) | 31 | 92 | $\nu$C=O: 1695 | 1.3 to 2.5 ppm, 8H, m; 2.8 to 3.3 ppm, 4H, m; 3.3 to 3.8 ppm, 3H, m; 3.9 to 4.7 ppm, 5H, m |
| 15 | —N(CH$_2$CH$_2$)$_2$O (morpholinyl) | 45 | 105 | $\nu$C=O: 1710 | 1.9 to 2.5 ppm, 2H, m; 3 to 4 ppm, 10H, m; 3.9 to 4.7 ppm, 6H, m |
| 16 | —N(CH$_2$CH$_2$)$_2$N—(2-methoxyphenyl), HCl | 38 | 165 | $\nu$C=O: 1715; $\nu$NH: 1900–2800 | 1.9 to 2.3 ppm, 2H, m; 3.3 to 4.7 ppm, 19H, m; 6.9 to 7.8 ppm, 4H, m; 6.5 ppm, exchangeable proton |
| 17 | —N(CH$_2$—CH$_2$Cl)$_2$ | 65 | 79 | $\nu$C=O: 1690 | 1.8 to 2.5 ppm, 2H, m; 2.5 to 3.9 ppm, 11H, m; 3.9 to 4.5 ppm, 3H, m |
| 18 | —N(CH$_2$CH$_2$)$_2$N—cyclohexyl | 64 | 121 | $\nu$C=O: 1720 | 0.8 to 2.3 ppm, 12H, m; 2.7 to 3.8 ppm, 12H, m; 3.8 to 4.7 ppm, 5H, m; 5.1 ppm, 2H, m, (exchangeable) |

TABLE 1-continued

| Compounds No. | R | Yield % | m.p. °C. | IR (cm$^{-1}$) | NMR |
|---|---|---|---|---|---|
| 19 | −N⌒N−(CH$_2$)$_3$−CH$_3$ | 50 | 92 | $\nu$C=O: 1650 and 1700 | 0.7 to 2.4 ppm, 9H, m; 2.7 to 4.6 ppm, 18H, m; 7.9 ppm, 2H, m, (exchangeable). |

We claim:

1. Oxaazaphosphorine compounds corresponding to the formula I

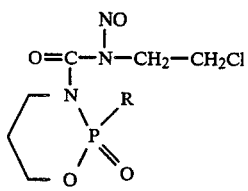

in which R is selected from the group consisting of:
straight-chain and branched-chain alkyl containing from 1 to 6 carbon atoms inclusive,
cycloalkyl containing from 3 to 7 carbon atoms inclusive,
unsubstituted phenyl and phenyl substituted by, a radical selected from the group consisting of alkyl and alkoxy each containing from 1 to 4 carbon atoms inclusive, and halogen
phenylalkyl containing from 7 to 10 carbon atoms inclusive, and these radicals substituted on the phenyl ring by a substituent selected from the group consisting of halogen and alkyl and alkoxy each containing from 1 to 4 carbon atoms inclusive,
straight-chain and branched-chain alkoxy, containing from 1 to 4 carbon atoms inclusive,
phenoxy and thiophenoxy,
mono- and di-alkylamino containing from 1 to 8 carbon atoms inclusive and these groups mono- and di-substituted by halogen, and
pyrrolidin-1-yl, morpholin-4-yl and piperid-1-yl groups, unsubstituted piperazin-1-yl and piperazin-1-yl substituted in the 4-position, by a substituent selected from the group consisting of straight-chain and branched-chain alkyl containing from 1 to 4 carbon atoms inclusive, cycloalkyl containing from 5 to 7 carbon atoms inclusive, unsubstituted phenyl and unsubstituted phenylalkyl containing from 7 to 10 carbon atoms inclusive, and these phenyl and phenylalkyl substituted on the aromatic ring, by a substituent selected from the group consisting of halogen and straight-chain and branched-chain alkyl and alkoxy each containing from 1 to 4 carbon atoms inclusive,
and also, when R is piperazinyl, their pharmaceutically acceptable acid addition salts.

2. Compounds according to claim 1 in which R is an amino group and, especially, a pyrrolidin-1-yl, piperid-1-yl or morpholin-4-yl radical, or a piperazin-1-yl radical that is optionally substituted by straight-chain or branched-chain alkyl containing from 1 to 4 carbon atoms inclusive, by cycloalkyl containing from 5 to 7 carbon atoms inclusive, or by phenyl or phenylalkyl that contains from 7 to 10 carbon atoms inclusive, in both of which the phenyl ring may be substituted by halogen or straight-chain or branched-chain alkyl or alkoxy each containing from 1 to 4 carbon atoms inclusive.

3. A compound of claim 1 which is 3-[N-(2-chloroethyl)-N-nitrosoamido]-2-(piperid-1-yl)-2-oxo-2H-tetrahydro-1,3,2-oxaazaphosphorine.

4. A compound of claim 1 which is 3-[N-(2-chloroethyl)-N-nitrosoamido]-2-(morpholin-4-yl)-2-oxo-2H-tetrahydro-1,3,2-oxaazaphosphorine.

5. A compound of claim 1 which is 3-[N-(2-chloroethyl)-N-nitrosoamido]-2-[1-(4-methylpiperazinyl)]-2-oxo-2H-tetrahydro-1,3,2-oxaazaphosphorine and its pharmaceutically acceptable acid addition salts.

6. A compound of claim 1 which is 3-[N-(2-chloroethyl)-N-nitrosoamido]-2-[4(4-methoxyphenyl)-piperazin-1-yl]-2-oxo-2H-tetrahydro-1,3,2-oxaazaphosphorine and its pharmaceutically acceptable acid addition salts.

7. Pharmaceutical compositions containing as active ingredient at least one compound according to claims 1, in combination with one or more inert non-toxic excipients.

8. Pharmaceutical compositions containing as active ingredient 3-[N-(2-chloroethyl)-N-nitrosoamido]-2-[1-(4-methylpiperazinyl]-2-oxo-2H-tetrahydro-1,3,2-oxaazaphosphorine or one of its pharmaceutically acceptable acide addition salts, in combination with one or more inert non-toxic excipients.

* * * * *

UNITED STATES PATENT AND TRADEMARK OFFICE
CERTIFICATE OF CORRECTION

PATENT NO. : 4,605,647
DATED : August 12, 1986
INVENTOR(S) : Gilbert Lavielle and Claude Cudennec It is certified that error appears in the above-identified patent and that said Letters Patent is hereby corrected as shown below:

Col. 2, line 21; "piperzinyl" should read -- piperazinyl --

Col. 4, line 59; "-oxaazaphosporine" should read
-- -oxaazaphosphorine --

Col. 6, line 3; "58%" should read -- 58%) --

Col. 11, Table 1-continued, Compound #4, under the "R" heading, in the formulation; "$CH_3$" should read -- N—$CH_3$ --

Col. 14, line 51; "acide" should read -- acid --

Signed and Sealed this

Tenth Day of February, 1987

*Attest:*

DONALD J. QUIGG

*Attesting Officer*     *Commissioner of Patents and Trademarks*